United States Patent [19]

Mudd

[11] 3,956,305
[45] May 11, 1976

[54] PHOSPHATED OXAZOLINES

[75] Inventor: Daniel G. Mudd, Mission Viejo, Calif.

[73] Assignee: Commercial Solvents Corporation, Terre Haute, Ind.

[22] Filed: May 8, 1975

[21] Appl. No.: 575,662

[52] U.S. Cl. ............... 260/307 F; 21/2.5 A; 21/2.7 A
[51] Int. Cl.² ........................ C07D 263/10
[58] Field of Search .................... 260/307 F

[56] References Cited
UNITED STATES PATENTS
2,965,459  12/1960  DeGray et al. ............... 44/63

Primary Examiner—Raymond V. Rush
Attorney, Agent, or Firm—Robert H. Dewey; Howard E. Post

[57] ABSTRACT

Phosphated derivatives of 4,4-bis(hydroxymethyl) oxazolines and process for preparation. The compounds are represented by the formula

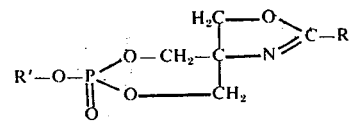

where R is alkyl or alkenyl of from 11 to 21 carbon atoms and R' is lower alkyl of 1 to about 5 carbon atoms. The products have utility as corrosion inhibitors in lube oils.

5 Claims, No Drawings

PHOSPHATED OXAZOLINES

BACKGROUND OF THE INVENTION

This invention relates to phosphated oxazolines. In a particular aspect, this invention relates to phosphated oxazolines having utility as corrosion inhibitors.

SUMMARY OF THE INVENTION

It is an object of this invention to provide phosphated oxazolines.

It is another object of this invention to provide a corrosion inhibitor soluble in lubricating oils.

Other objects will be apparent to those skilled in the art from the disclosure herein.

It is the discovery of the present invention to provide compounds represented by the formula

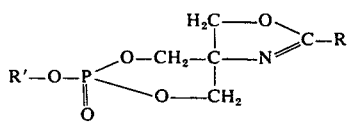 (I)

where R is alkyl or alkenyl of from 11 to 21 carbon atoms and R' is lower alkyl of 1 to about 5 carbon atoms. The products are effective, oil-soluble corrosion inhibitors.

DETAILED DISCUSSION

The phosphated oxazolines of the present invention are prepared by reacting an oxazoline represented by the formula

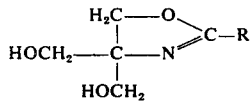 (II)

wherein R has the same meaning hereinbefore set forth with a tri-alkyl phosphite, the alkyl group having from 1 to 5 carbon atoms, thereby forming the mono alkyl phosphite ester of the oxazoline. This compound is then oxidized to produce the phosphate compound, I.

The oxazolines employed in the practice of this invention are known from R. F. Purcell, U.S. Pat. No. 3,248,397, and some of them are commercially available. The preferred oxazoline is the one corresponding to II wherein R is an alkenyl group of 17 carbon atoms.

The alkyl phosphite esters used in the practice of this invention are also known in the art, and at least some are commercially available. Triethyl phosphite is preferred.

These compounds are soluble in lubricating oils and are useful as corrosion inhibitors in a concentration of from about 0.1% to about 5% by weight.

The invention can be better understood by reference to the following examples. It is understood however that the examples are intended for illustration only and it is not intended that the invention be limited thereby.

EXAMPLE 1

To a reaction vessel there was delivered 4,4-bis-(hydroxymethyl)-2-heptadecenyl-2-oxazoline 364 g (1 mole). The reaction vessel was equipped with a heat source, a nitrogen purge, Vigreux column with a Dean-Stark trap, a condenser and an agitator. Triethyl phosphite 166 g (1 mole) and triethylamine catalyst, 5 drops (about 0.1–0.2 g) were added. The mixture was heated to 170°C with agitation while continuously purging with nitrogen. After about 84 ml of ethanol was collected in the trap, the nitrogen purge was discontinued, the heat was removed and the contents were allowed to cool to 100°C. Oxygen from an oxygen supply was then passed through the reaction mixture for 6 hours. There was obtained the mono-ethyl phosphate ester of the oxazoline.

The product contained 3.10% nitrogen compared with a calculated value of 3.08% for the expected product. The infra-red absorption spectrum showed a characteristic P=O peak at 1280 cm$^{-1}$ and the product was light colored. The yield was 81% as determined from the ethanol removed. The product was soluble in lubricating oil up to a concentration of 25% by weight at 0°C.

Test solutions of lubricating oil free from other additives and corrosion inhibitors are prepared containing the mono-ethyl phosphate ester at concentrations of 0.1%, 0.25%, 0.5% and 1.0%. They are tested by known methods, of which there are many, and all are determined to exhibit corrosion inhibition on steel.

EXAMPLE 2

The experiment of Example 1 was repeated in all essential details except that tributyl phosphite was substituted for triethyl phosphite in equi-molar amounts. The monobutyl phosphate oxazoline ester thereby obtained was dark colored.

EXAMPLE 3

The experiment of Example 1 is repeated in all essential details except that 4,4-bis(hydroxymethyl)-2-undecanyl-2-oxazoline was substituted for the oxazoline of Example 1 on an equi-molar basis. The mono-ethyl phosphate oxazoline ester thereby obtained exhibits corrosion inhibition on steel when incorporated in a lubricating oil at concentrations of 0.1% to 1.0%.

EXAMPLE 4

The experiment of Example 1 is repeated in all essential details except that 4,4-bis(hydroxymethyl)-2-heneicosyl-2-oxazoline was substituted for the oxazoline of Example 1 on an equi-molar basis. The mono-ethyl phosphate oxazoline ester thereby obtained exhibits corrosion inhibition on steel when incorporated in a lubricating oil at concentrations of 0.1% to 1.0%.

I claim:

1. A phosphated oxazoline of the formula

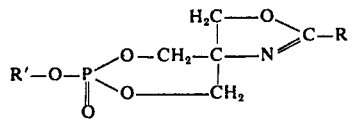

where R is alkyl or alkenyl of from 11 to 21 carbon atoms and R' is alkyl of from 1 to 5 carbon atoms.

2. A phosphated oxazoline of claim 1 wherein R is heptadecenyl.

3. A phosphated oxazoline of claim 1 wherein R is undecanyl.

4. A phosphated oxazoline of claim 1 wherein R is heneicosyl.

5. A phosphated oxazoline of claim 1 wherein R' is ethyl.

* * * * *